(12) United States Patent
Royster, Jr.

(10) Patent No.: US 9,457,022 B2
(45) Date of Patent: *Oct. 4, 2016

(54) METHODS AND COMPOSITIONS FOR TREATING OR PREVENTING SYMPTOMS OF HORMONAL VARIATIONS

(71) Applicant: FERVENT PHARMACEUTICALS, LLC, Greenville, NC (US)

(72) Inventor: George R. Royster, Jr., Greenville, NC (US)

(73) Assignee: FERVENT PHARMACEUTICALS, LLC, Greenville, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/705,087

(22) Filed: May 6, 2015

(65) Prior Publication Data

US 2015/0231129 A1    Aug. 20, 2015

Related U.S. Application Data

(63) Continuation of application No. 14/483,653, filed on Sep. 11, 2014, now abandoned, which is a continuation of application No. 13/886,860, filed on May 3, 2013, now abandoned, which is a continuation of application No. 13/343,515, filed on Jan. 4, 2012, now Pat. No. 8,461,102, which is a continuation-in-part of application No. 13/037,728, filed on Mar. 1, 2011, now abandoned.

(60) Provisional application No. 61/309,638, filed on Mar. 2, 2010.

(51) Int. Cl.
*A61K 31/47*      (2006.01)
*A61K 31/4748*   (2006.01)
*A61K 31/195*    (2006.01)
*A61K 45/06*     (2006.01)

(52) U.S. Cl.
CPC ......... *A61K 31/4748* (2013.01); *A61K 31/195* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 3,119,742 A * | 1/1964 | MacDonnell et al. | 424/498 |
| 6,310,098 B1 * | 10/2001 | Guttuso, Jr. | A61K 31/138 514/567 |
| 6,335,030 B1 * | 1/2002 | Hoeck et al. | 424/449 |
| 8,461,102 B2 * | 6/2013 | Royster, Jr. | 514/1 |
| 2005/0129783 A1 * | 6/2005 | McCleary | A23L 1/3002 424/646 |

OTHER PUBLICATIONS

Hormones in Men and How Male Hormones change over time, accessed online Oct. 15, 2014.*
Drugs and Human Performance Fact Sheets—Dextromethorphan, accessed online Oct. 17, 2014.*

* cited by examiner

*Primary Examiner* — Robert A Wax
*Assistant Examiner* — Melissa Mercier
(74) *Attorney, Agent, or Firm* — Ward and Smith, P.A.; Jeffrey W. Childers

(57) ABSTRACT

The present invention relates to methods, compositions, and kits for treating or preventing symptoms of hormonal variation. The method comprises the steps of administering an effective amount of Dextromethorphan or Dextrorphan, or a pharmaceutically acceptable salt thereof, to a subject having one or more symptoms of hormonal variations.

5 Claims, No Drawings

METHODS AND COMPOSITIONS FOR TREATING OR PREVENTING SYMPTOMS OF HORMONAL VARIATIONS

CROSS REFERENCE TO RELATED APPLICATIONS

This application is a Continuation application of U.S. patent application Ser. No. 14/483,653, filed Sep. 11, 2014, which is a Continuation application of U.S. patent application Ser. No. 13/886,860, filed May 3, 2013, which is a Continuation application of U.S. patent application Ser. No. 13/343,515, filed Jan. 4, 2012, and now issued U.S. Pat. No. 8,461,102 issued on Jun. 11, 2013, which is a Continuation-in-Part application of U.S. patent application Ser. No. 13/037,728, filed Mar. 1, 2011, which is related to and claims priority to U.S. Provisional Application Ser. No. 61/309,638 filed Mar. 2, 2010, entitled "Methods and Compositions for Treating or Preventing Symptoms of Hormonal Variations," the content of each of the aforementioned applications is herein incorporated by reference in its entirety.

FIELD OF THE INVENTION

The present invention relates generally to methods, compositions, and kits for treatment or prevention of symptoms of hormonal variation associated with menopause, surgery, anti-estrogen drugs and/or androgen deprivation therapy, such as hot flashes, night sweats, and insomnia.

BACKGROUND OF THE INVENTION

Hot flashes are the most common symptoms experienced by women who are perimenopausal or postmenopausal and are also found in men with prostate cancer who undergo androgen deprivation therapy (ADT). Hot flashes are generally systemic and likely result from an alteration in the thermoregulatory set-point center, which is located in the pre-optic anterior hypothalamus, with involvement of dopamine, serotonin, norepinephrine, and their respective receptors.

Symptoms of hot flashes include a sudden sensation of warmth, which are usually accompanied by skin reddening, perspiration, palpitation, anxiety, irritability, and even panic and night sweats. They can be characterized by mild warmth to profuse sweating. Typical hot flashes occur with sudden onsets of sensation of warmth in the chest, which then spreads upward to involve the neck and face. Other people feel a sudden onset of warmth all over the upper part of the body. A chill may follow a hot flash because of a subsequent drop in core temperature. Hot flashes may also be accompanied by dizziness, nausea, headaches, palpitations, and profuse sweating. Such symptoms can disrupt sleep and work and interfere with quality of life.

The severity of hot flash sensations varies greatly both from time to time in the same person and from person to person. Hot flashes have been studied in perimenopausal and postmenopausal women but have not been studied extensively in men. Hot flashes in a woman can occur several times a week to as frequently as once an hour. Each episode can last from a few seconds to sixty minutes, depending on the woman. Hot flashes are provoked by several factors such as hot weather, stress, eating, or drinking alcohol. The severity and length of hot flashes can result in sleep deprivation and interference with work and lifestyle.

Perimenopausal and postmenopausal women are likely to have hot flashes. In fact, almost 60-70% of postmenopausal women have hot flashes, and approximately 10-20% of all postmenopausal women will report intolerable symptoms. Some women may suffer from these symptoms for up to 15 years. Thus, the identification and proper management of menopausal and postmenopausal symptoms are crucial to maintaining a woman's quality of life.

Hot flashes are also a common and potentially chronic problem in men. For example, men with prostate cancer who undergo ADT may have hot flashes. This is a major quality of life issue for a significant proportion of men receiving ADT. One report shows that the natural history of hot flashes in men, including variation in severity and frequency, has not been widely studied. It is known that almost 70% of men who undergo surgical orchiectomy report hot flashes. About 70 to 80% of men on long-term androgen suppression have hot flashes, and 30 to 40% of these patients report that symptoms are a major source of discomfort.

Although the pathophysiology of hot flashes is not completely understood, it has been postulated that hot flashes result from a transient lowering of the hypothalamic temperature regulatory set point. Because of the temporal relation between changes in sexual hormone concentrations and the onset of hot flashes, it is believed that such symptoms result from declining estrogen levels or increased gonadotropin concentrations. Thus, hot flashes occur commonly in menopausal women, but also occur in premenopausal women taking anti-estrogen drugs, such as tamoxifen. Administration of aromatase inhibitors, which are anti-estrogen drugs given to menopausal women with a history of breast cancer, also can result in hot flashes as a side effect. Men on androgen deprivation treatment may also experience such symptoms.

Although estrogen replacement therapy can effectively minimize or prevent hot flashes in women, many women are concerned about potential risks of hormone replacement therapy. This is especially true for women who suffer from breast cancer or have a family history of breast cancer, and/or a history of clotting disorders.

Various non-hormonal agents for treating the symptoms of hot flashes have been tested. One of these agents is clonidine, a centrally-acting $alpha_2$ adrenergic receptor agonist. It selectively stimulates receptors in the brain that monitor catecholamine levels in the blood. These receptors close a negative feedback loop that begins with descending sympathetic nerves from the brain that control the production of catecholamines (e.g., epinephrine, also known as adrenaline, and norepinephrine) in the adrenal medulla. By tricking the brain into believing that catecholamine levels are higher than they really are, clonidine causes the brain to reduce its signals to the adrenal medulla, leading to lower catecholamine production. The result is a lowered heart rate and blood pressure. In randomized clinical trials, clonidine was shown to be moderately more efficacious than placebo in preventing hot flashes, but adverse effects were common, including dry mouth, dizziness, and blurred vision.

There are also a number of treatments for hot flashes that appeared to have similar effects in men and women. Decreases of hot flash frequencies in women treated with clonidine are approximately 10-15 percent greater than that seen with placebo. In a double blind, cross over study of clonidine to reduce self-reported hot flash frequency in men, a similar effect was seen, but the difference from placebo effect was not statistically significant. Research has found virtually identical results for men and women receiving megestrol acetate for hot flashes, with approximately an 80% reduction in self-reported hot flash frequency compared to a 20% reduction with placebo. However, higher levels of vaginal bleeding were also associated with the use of megestrol acetate in women.

Many women seek complementary and alternative medicine (CAM) methods to ease their menopausal symptoms. Compounds used as complementary and alternative medicine include Soy Vitamin E, Red clover (*Trifolium pratense*), dong quai, evening primrose oil, and black cohosh (*Cimicifuga racemosa*).

Over the last few years, anecdotal reports suggested that antidepressants from the SSRI/SNRI groups might reduce symptoms of hot flashes. These observations led to initial pilot studies and then to randomized placebo controlled clinical trials. In pilot studies, the SNRI venlafaxine (Effexor) and the SSRI paroxetine (Paxil) were associated with hot-flash score reductions on the order of 55%-75%. Other pilot evaluations have suggested that citalopram (Celexa) and mirtazapine (Remeron) also alleviate hot flashes to a similar degree. The first reported randomized clinical trial of one of these newer antidepressants compared three doses of venlafaxine (37.5, 75, and 150 mg/day) to placebo. While low-dose venlafaxine was only mildly more effective than placebo (37% vs 27% reduction in hot-flash scores, respectively), both the moderate and high doses were associated with a statistically significant 61% reduction in hot flash scores. Fluoxetine (Prozac) 20 mg/day was associated with a 50% reduction in hot-flash scores compared to a 36% reduction with placebo. Adverse effects with SSRIs are moderate, including headache, agitation, tremor, sedation, and sexual dysfunction.

More recently, anecdotal observations suggesting efficacy led to trials to assess the value of another compound, gabapentin (Neurontin™). Gabapentin is a γ-aminobutyric acid (GABA) analog that has been most often prescribed for the treatment of seizures and naturopathic pain. It is also effective in other syndromes, such as panic disorder, social phobia, migraine headache, and essential tremor. Based on anecdotal observations, pilot and randomized trials of gabapentin for the treatment of hot flashes were launched. Results of the pilot trials suggested that gabapentin reduces the incidence of hot flashes by 42%-70%. Benefit was demonstrated regardless of the concurrent use of a stable dose of an SSRI/SNRI agent.

Serada™, another formulation of gabapentin, has also been tested in clinical trials for the treatment of menopausal hot flashes. Serada™ dosed once daily (1200 mg) or twice daily (600 mg in the morning and 1200 mg in the evening for a total of 1800 mg) resulted in a significant reduction of frequency and severity of hot flashes measured after four weeks. However, this effect was not found after 12 weeks of usage.

Given the risks of estrogen replacement therapy and marginal benefits of current non-hormonal treatments, there is a continued need for alternative methods or compositions such as drugs for treating or preventing symptoms associated with menopause, surgery, anti-estrogen drugs, and/or androgen deprivation therapy, including hot flashes. In accordance with the invention, such an alternative method and compositions are provided which avoid the dangers of estrogen replacement therapy while providing for an effective treatment of symptoms.

SUMMARY OF THE INVENTION

The present invention provides methods and compositions for treatment and prevention of symptoms of hormonal variation. Specifically, the invention relates to symptoms associated with menopause, surgery, anti-estrogen drugs, and/or androgen deprivation therapy, such as hot flashes, night sweats, and insomnia, which are frequently experienced by both males and females.

In one aspect, the invention relates to methods for treating or preventing symptoms of hormonal variation, particularly associated with menopause, surgery, anti-estrogen drugs, and/or androgen deprivation therapy. The method generally includes: identifying a subject having one or more symptoms of hormonal variations, and administering an effective amount of a pharmacologically active agent which modulates the activity of dopamine, norepinephrine and/or serotonin in the brain to prevent or reduce both the frequency and severity of hot flashes. Such an agent may act indirectly by modifying dopamine, norepinephrine or serotonin activity secondary to inhibiting the transport of serotonin and/or norepinephrine in the brain. In a preferred embodiment, the agent is one selected from Dextromethorphan, e.g., Dextromethorphan HBR, or Dextrorphan, or a pharmaceutically acceptable salt thereof.

In a second aspect, the invention relates to a pharmaceutical composition for treating or preventing symptoms of hormonal variation. The pharmaceutical composition includes an effective amount of a pharmacologically active agent for treating or preventing symptoms of hormonal variation, wherein the agent binds to the NMDA receptor and thereby modifies the activity of dopamine and/or serotonin and at least one receptor selected from a serotonin type 2A ($5\text{-HT}_{2A}$) receptor and a dopamine type 2 ($D_2$) receptor. As discussed above, in a preferred embodiment, the agent is one selected from Dextromethorphan, e.g., Dextromethorphan HBR, or Dextrorphan, or a pharmaceutically acceptable salt thereof.

In a third aspect, the invention is directed to kits for performing a method of the invention. Typically, the kits of the invention comprise a presently disclosed pharmacologically active agent, such as Dextromethorphan, e.g., Dextromethorphan HBR, or Dextrorphan, or a pharmaceutically acceptable salt thereof, for treating or preventing symptoms of hormonal variation and instructions for a method of the invention. The kits can also comprise some or all of the other reagents and supplies necessary to perform at least one embodiment of one method of the invention.

These and other advantages and features that characterize the invention are set forth in the claims annexed hereto and forming a further part hereof. However, for a better understanding of the invention, and of the advantages and objectives attained through its use, reference should be made to the accompanying descriptive matter, in which there are described exemplary embodiments of the invention.

DETAILED DESCRIPTION OF THE INVENTION

The present invention relates to methods, compositions, and kits for treating or preventing symptoms associated with hormonal variations, particularly those associated with hormonal changes accompanying menopause, surgery, anti-estrogen drugs and/or androgen deprivation therapy. Specifically, the inventor has surprisingly found that pharmacologically active agents commonly used as antitussive (cough suppressant) drugs, can be used to treat or prevent symptoms associated with hormonal variations.

Accordingly, in one aspect, the invention provides methods for treating or preventing symptoms of hormonal variation, particularly associated with perimenopause, menopause, surgery, anti-estrogen drugs, and/or androgen deprivation therapy. The methods include identifying a subject having one or more symptoms of hormonal variations, and administering an effective amount of Dextromethorphan, e.g., Dextromethorphan HBr, or Dextrorphan, or a pharmaceutically acceptable salt thereof to the subject.

In a preferred embodiment, the agent is Dextromethorphan, DextromethorphanHBr or Dextrorphan. Dextromethorphan is the dextrorotatory enantiomer of the methyl ether of levorphanol, an opiod analgesic. Dextromethorphan is rapidly absorbed from the gastrointestinal tract, where it enters the bloodstream and crosses the blood-brain barrier. Dextromethorphan is known to be both a serotonin transport and a norepinephrine transport blocker. After absorption from the gastrointestinal tract, Dextromethorphan is converted into the active metabolite Dextrorphan in the liver by CYP2D6, a cytochrome P450 enzyme. Dextrorphan is an active metabolite of Dextromethorphan and the therapeutic activity of Dextromethorphan is believed to be caused by both the drug and this metabolite.

Dextromethorphan HBr is a specific form of Dextromethorphan. HBr, i.e. hydrobromide, refers to hydrobromic acid which is mainly used for the production of inorganic bromides, especially the bromides of zinc, calcium, and sodium. While reference is made to Dextromethorphan-HBr as a specific form of Dextromethorphan used in the invention, it will be readily apparent to those of ordinary skill that other forms can be used. More particularly, one of ordinary skill in the art would recognize that other pharmaceutically acceptable salts of dextromethorphan or dextrorphan are suitable for use with the presently disclosed subject matter.

As used herein, the term "pharmaceutically acceptable salt" is meant to include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids including, but not limited to, hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like {see, for example, Berge et al, "Pharmaceutical Salts", Journal of Pharmaceutical Science, 1977, 66, 1-19). In particular embodiments, the pharmaceutically acceptable salt is an acid addition salt.

The methods of the invention can be used on male or female subjects. It is envisioned that the methods will be used for subjects that are prone to having, are currently having, or are expected to have symptoms of hormonal variation. These include subjects that are in perimenopause, menopause, anticipating or have gone through surgery, androgen deprivation therapy or chemotherapy, subjects that are being given Goserelin (such as Zoladex™) or Leuprolide (such as Lupron™) to induce menopause, subjects that are taking anti-estrogen drugs (such as tamoxifin or aromatase inhibitors), and/or any other condition that results in changes in hormonal levels.

The symptoms of hormonal variation include a sudden sensation of warmth, which are usually accompanied by skin reddening, perspiration, palpitation, anxiety, irritability, and even panic and night sweats. A chill may follow a hot flash because of a subsequent drop in core temperature. Hot flashes may also be accompanied by dizziness, nausea, headaches, palpitations, and profuse sweating. Although any of these symptoms can be alleviated or prevented by the methods of the invention, it is expected that the methods will reduce or prevent hot flashes, which will result in a reduction, elimination, or prevention of the symptoms caused by the hot flashes.

In accordance with some embodiments of the invention, a method for treating or preventing symptoms of hormonal variations may comprise the use of an effective amount of Dextromethorphan, e.g., DextromethorphanHBr, or Dextrorphan, or a pharmaceutically acceptable salt thereof. An effective amount of Dextromethorphan, e.g., DextromethorphanHBr, or Dextrorphan, or a pharmaceutically acceptable salt thereof, will depend on the mode of administration, frequency of administration, and the type of pharmaceutical composition used to deliver the compound into a patient, as well as weight, gender, age, and physical conditions of the patient.

Generally, effective amounts of such compounds will be about 0.002 mg to about 1.0 mg/kg body weight per day, preferably about 0.005 mg to 1.0 mg/kg body weight per day, and more preferably about 0.005 to about 0.7 mg/kg body weight per day. For example, daily doses may range from about 0.1 to about 50 mg per day for an adult patient weighing about 50 Kg (110 lb), or from about 0.2 to about 100 mg per day for an adult patient weighing about 100 Kg (220 lb). In one preferred embodiment, approximately 30 to approximately 45 mg per day of Dextromethorphan, DextromethorphanHBr or Dextrorphan, or a pharmaceutically acceptable salt thereof, is administered to a subject. It is expected that no more than 120 mg of a daily dose will be administered, although depending on the mode of administration, frequency of administration, and the type of pharmaceutical composition used to deliver the compound into a patient, as well as the weight, gender, age, and physical conditions of the patient, one of ordinary skill in the art would appreciate that the daily maximum dose administered to the patient can, in some embodiments, exceed 120 mg. Typically, 100 mg will be the maximum daily dose required in most cases for the methods of the present invention. While individual needs vary, determination of optimal range of effective amounts of each compound is within the skills of one skilled in the art. By treating the symptoms of hormonal variations, including hot flashes, embodiments of the invention either reduce the number (occurrence or frequency), duration, and/or severity of symptomatic events.

Administering an effective amount of a compound of the invention to a patient may be via any suitable route used for administering similar pharmaceuticals to a patient, including oral administration (such as a solution, gel, tablet, capsule, and powder), injection, suppository, infusible, lozenge, cream, salve, inhalant, transdermal patch, and the like. The compound may be administered with any substance that is biologically tolerable (i.e., non-toxic or present in an amount that is non-toxic). Examples of such substances are well known to those of skill in the art and include, without limitation, sugars, salts, lipids, drugs, excipients, carriers, flavorants, fillers, binders, gums, colorants, water, buffers, detergents, biologically active compounds, and the like.

Administration of an effective amount of a compound of the invention to a subject may be in one dose or the method may comprise two or more administrations of less than the effective amount, where the amount ultimately administered is an effective amount. For example, if 30 mg per day is to be administered, one dose of 30 mg may be given, two doses of 15 mg may be given, three doses of 10 mg may be given in one day, etc. Likewise, multiple administrations of an effective dose may be desirable where the second or subsequent administration is performed at a time well separated from the first administration. In addition, it may be desired to administer the effective dose using a slow release method (also called time, sustained, or extended release) instead of an immediate release. In this case, the total effective amount is administered but the compound of the invention is released systemically in the subject over hours instead of minutes.

The effective amount of a compound of the invention to a subject may be lower if one or more other compounds that reduce the symptoms of hormonal variation are concurrently given to a subject. These compounds include, but are not limited to, compounds used as complementary and alternative medicine such as Soy Vitamin E, Red clover (*Trifolium pratense*), dong quai, evening primrose oil, and black cohosh (*Cimicifuga racemosa*). These compounds may also include medicines considered mainstream including, but not limited to, conjugated estrogens (i.e., a kind of hormone replacement therapy, i.e., "HRT", such as Cenestin™, Enjuvia™, and Premarin™), bupropian (such as Wellbutrin™, Zyban™, Aplenzin™, and Budeprion™), venlafaxine (such as Effexor™), fluoxetine (such as Prozac™, Rapiflux™, and Sarafen™), duloxetine (such as Cymbalta™), sertraline (such as Zoloft™), clonidine (such as Catapres-TTS-1™, Catapres-TTS-2™, and Catapres-TTS-3™), clonidine hydrochloride, methyldopa (such as Aldomet™), and gabapentin (such as Neurontin™ and Serada™). If a compound of the invention is given to a subject along with one or more other compounds known to reduce the symptoms of hormonal variation, then the effective amount of the compound of the invention may be lower than if the compound of the invention is administered alone. The effective amount of the compound of the invention may then be, for example, one-half, one-third, one-fourth, one-sixth, or one-eighth of the effective amount of the compound when given by itself.

In accordance with one exemplary embodiment of the invention, Dextromethorphan, e.g., Dextromethorphan HBr, or a pharmaceutically acceptable salt thereof, may be used to treat symptoms of hormonal variations. Dextromethorphan, e.g., Dextromethorphan HBr, is an antitussive (cough suppressant) drug that functions by interfering with the communication among nerves in the brain. It elevates the threshold for coughing, without inhibiting ciliary activity. However, as described herein, Dextromethorphan, e.g., Dextromethorphan HBr, has been unexpectedly found to be effective in reducing or eliminating symptoms associated with hormonal variations.

In accordance with another embodiment of the invention, Dextrorphan may be used as a treatment for the symptoms of hormonal variations. Dextrorphan is the principal active metabolite of Dextromethorphan, e.g., Dextromethorphan HBr. Like Dextromethorphan, e.g., Dextromethorphan HBr, Dextrorphan can effectively treat or prevent the symptoms associated with hormonal variations.

In a second aspect, the invention relates to pharmaceutical compositions for treating or preventing symptoms of hormonal variation. The pharmaceutical composition is comprised of an effective amount of Dextromethorphan, e.g., Dextromethorphan HBr, or Dextrorphan, or a pharmaceutically acceptable salt thereof, for treating or preventing symptoms of hormonal variation.

The pharmaceutical composition can be a pharmaceutically acceptable form such as an oral dosage form, injection, inhalation, and/or transdermal patch. In some embodiments, the pharmacologically active agent, e.g., Dextromethorphan, e.g., Dextromethorphan HBR, or Dextrorphan, or a pharmaceutically acceptable salt thereof, is in a controlled-release or extended-release or sustained-release dosage form, including, but not limited to, those controlled-release or extended-release or sustained-release dosage forms disclosed in U.S. Pat. Nos. 7,897,080; 7,871,645; 6,607,748; 6,589,551; 6,528,080; 6,500,459; 6,461,631; 6,309,669; 6,117,452; 5,700,478; 5,700,410; 5,536,505; 5,523,095; 5,518,730; 5,445,829; 5,368,852; 5,288,503; 5,133,974; 5,084,278; 4,996,047; 4,983,401; 4,952,402; 4,834,965; 4,800,087; and 4,788,055, and U.S. Patent Application Publication Nos. 20110217371, 20110081419, 20100151022, 20100092545, 20090155355, 20090047336, 20090022807, 20090004281, 20080286344, 20080286343, 20060240107, 20060193877, 20060013876, 20060008527, 20050265955, 20040185097, 20030180362, 20030099711, and 20020090398, each of which is incorporated herein by reference in their entirety.

Representative transdermal delivery devices are disclosed in U.S. Pat. Nos. 7,829,116; 7,767,656; 6,365,178; 6,335,030; and 5,260,066, each of which is incorporated herein by reference in its entirety.

In some embodiments, oral dosage forms, for example, may be a controlled-release dosage form, rapidly dispersed dosage form with a porous network of a matrix composition, or a solid rapidly disintegrating dosage form. For example, an oral dosage form may be made up of a microparticle composition and a biodegradable and biocompatibly acceptable microparticle polymer carrier. One oral dosage form may include at least a sustained-release microparticle produced by dissolving in a solvent with a biodegradable and biocompatible polymer to form an organic phase, and extracting the solvent to form microparticles. Another oral dosage form may be a microencapsulated pharmaceutical composition having a selected release profile prepared by a method for preparing microparticles.

The method of preparing microparticles may involve: (a) preparing an emulsion that has a first phase and a second phase, wherein the first phase includes the active agent, a polymer, and a solvent for the polymer; (b) quenching the emulsion in a quench liquid to form microparticles containing the active agent; (c) selecting a degree of intermediate drying of the microparticles to be performed so that the selected release profile is achieved; (d) washing the microparticles; and (e) conducting final drying of the microparticles.

The oral dosage form can be a multi-phasic sustained-release microparticle composition, prepared by a process involving: dissolving in a solvent the active agents and a biodegradable and biocompatible polymer to form an organic phase; extracting the solvent to form microparticles; and combining microparticles having a plurality of sizes to thereby form a composition that delivers the active agent in a multi-phasic manner.

A pharmaceutical composition optionally includes the active agents, and at least one substance selected from pharmaceutically acceptable carriers, nutrients, vitamins, other active ingredients, sweeteners, flavoring agents, coloring agents, surfactants, preservatives, antioxidants, viscosity enhancers, and minerals. As used herein, "pharmaceutically acceptable" is intended to include ingredients that are biologically tolerable. As used herein, "biologically tolerable" means substances that are non-toxic to humans. The use of such ingredients is well known in the art, and thus further examples and methods of incorporating each into compositions at effective levels need not be discussed here. As used herein, "pharmaceutically acceptable carrier" refers to solvents, binders, disintegrating agents, lubricants, excipients, absorption delaying agents, and the like.

In a third aspect, the present invention is directed to kits for performing a method of the invention. Typically, the kits of the invention comprise a presently disclosed pharmacologically active agent, such as Dextromethorphan, e.g., Dextromethorphan HBR, or Dextrorphan, and instructions for how to perform at least one method of the invention. The pharmacologically active agent is generally supplied in the kits in an amount sufficient to treat at least one patient at least one time to reduce, eliminate, or prevent the symptoms of hormonal variations. Alternatively, the kit can be comprised of a dose of a pharmacologically active agent wherein the dose is not enough to be effective for reduction, elimination, or prevention of the symptoms of hormonal variations by itself, but when administered with another dose at a later time, it becomes effective. The pharmacologically active agent supplied in the kits may be supplied as a solution, gel, tablet, capsule, powder, injection, suppository, infusible, lozenge, cream, salve, inhalant, transdermal patch, and the like. The kits can also comprise some or all of the other reagents and supplies necessary to perform at least one embodiment of one method of the invention.

In its simplest form, a kit according to the invention comprises a container containing at least one type of pharmacologically active agentor at least one composition according to the invention. Thus, in embodiments, the kit of the invention comprises a container containing at least one type of pharmacologically active agent or a composition comprising a pharmacologically active agent. In other embodiments, the kit comprises multiple containers, each of which may contain at least one pharmacologically active agent, compositions comprising pharmacologically active agents, or other substances that are useful for performing one or more embodiments of the invention.

The container can be any material suitable for containing a composition of the invention or another substance useful in performing a method of the invention. Thus, the container may be a vial or ampule. It can be fabricated from any suitable material, such as glass, plastic, metal, or paper or a paper product. In embodiments, it is a glass or plastic ampule or vial that can be sealed, such as by a stopper, a stopper and crimp seal, or a plastic or metal cap. In embodiments, the container comprises an effective amount of pharmacologically active agent to reduce, eliminate, or prevent the symptoms of hormonal variation according to the invention. The amount of pharmacologically active agent contained in the container can be selected by one of skill in the art without undue experimentation based on numerous parameters that are relevant according to the invention.

In embodiments, the container is provided as a component of a larger unit that typically comprises packaging materials (referred to below as a kit for simplicity purposes). The kit of the invention can include suitable packaging and instructions and/or other information relating to the use of the compositions. Typically, the kit is fabricated from a sturdy material, such as cardboard and plastic, and can contain the instructions or other information printed directly on it. The kit can comprise multiple containers containing the composition of the invention. In such kits, each container can be the same size, and contain the same amount of composition, as each other container, or different containers may be different sizes and/or contain different amounts of compositions or compositions having different constituents. One of skill in the art will immediately appreciate that numerous different configurations of container sizes and contents are envisioned by this invention, and thus not all permutations need be specifically recited herein.

In general, the kit comprises containers to contain the components of the kit, and is considered a single package comprising a combination of containers. Thus, the components are said to be in packaged combination within the kit. In addition to a container containing the composition of the invention, the kit can comprise additional containers containing additional compositions of the invention. Each container may contain enough pharmacologically active agent for a single dose of an embodiment of the method of the invention, or it may contain enough for two or more doses. The various containers may contain differing amounts of the composition of the invention. Thus, in embodiments, the kit comprises a sufficient amount of pharmacologically active agent to perform an embodiment of the method according to the invention. The kit can further comprise some or all of the supplies and materials needed to prepare for and perform a method of the invention, such as, but not limited to, syringes, sterile water or a sterile aqueous solution. In some embodiments, the kits comprise one or more liquids to hydrate the compositions of the kits.

EXAMPLES

The following examples are provided to illustrate that embodiments of the present invention can reduce the symptoms of hormone variations, including hot flashes, night sweats, and blood pressure fluctuations. Embodiments of the invention are effective for patients under various conditions. However, one of ordinary skill in the art would appreciate that these examples are for illustration purposes only and by no means is intended to limit the scope of the invention.

Example 1

Dextromethorphan, e.g., DextromethorphanHBr Resolved Hot Flashes in a Case Involving a Partial Hysterectomy, Hormone Replacement Therapy and Breast Cancer Surgery/Treatment As previously noted, embodiments of the invention involve administering a therapeutically effective amount of an pharmacologically active agent, such as Dextromethorphan, e.g., Dextromethorphan HBr or Dextrorphan, to alleviate symptoms associated with hormone variations. This example involves use of Dextromethorphan HBr which has been used on a patient with a breast cancer history to successfully alleviate the occurrence of hot flashes or other symptoms of hormonal variations. The following describes a real specific past example of use of the methods and compositions of the invention with one patient, illustrating the effectiveness of Dextromethorphan, e.g., DextromethorphanHBr in alleviating symptoms associated with hormone variations. The following example from one patient illustrates the effectiveness of Dextromethorphan, e.g., Dextromethorphan HBr in alleviating symptoms associated with hormone variations. One of ordinary skill in the art would appreciate that this specific example is not intended to limit the scope of the invention.

In September of 1993, a 31-year-old woman who had been experiencing severe menstrual cycles required a partial hysterectomy. Within a few months of the surgery, she started to experience hot flashes, night sweats and insomnia. These occurrences took place several times a day/night lasting a few minutes. Approximately a year after surgery, she was placed on Cenestin™ (a kind of hormone replacement therapy, i.e., "HRT"). Upon starting the Cenestin™, the patient reported that the frequency and intensity of her hot flashes were reduced. In 2006, the Cenestin™ was discontinued due to an increase in hot flashes, night sweats and irritability.

At this time, the patient began taking dosages of Wellbutrin™ and receiving another hormone replacement therapy of estrogen and testosterone to treat the hot flashes, night sweats and other menopausal symptoms. Upon starting this new therapy, the patient reported that the frequency and intensity of her hot flashes, night sweats and other menopausal symptoms were markedly reduced.

In November of 2008, at the age of 46, the patient was diagnosed with Stage 2 breast cancer and the HRT was discontinued immediately. Subsequently, the patient underwent a lumpectomy and the removal of fourteen lymph nodes (one tested positive). At this time, the menopausal symptoms returned.

In December 2008, the patient went through an intense treatment of chemotherapy which lasted until April 2009. At this time, a less intense chemotherapy treatment was continued until November 2009. The patient also received radiation therapy from April 2009 until June 2009. At the end of the radiation therapy, the patient was started on a regimen of Tamoxifen™. Since commencing treatment with Tamoxifen™, the hot flashes, night sweats and other menopausal symptoms increased in intensity.

In February 2009, the patient was treated with Vitamin E and Clonidine™, a blood pressure medication that has also been used to reduce menopausal symptoms. Clonidine™ is a direct-acting α2 adrenergic agonist that is used to treat several medical conditions. The Clonidine™ had no impact on reducing the menopausal symptoms. Both the Clonidine™ and the Wellbutrin™ were discontinued in June 2009.

In June 2009, the patient was treated with Neurontin™ (generic name gabapentin), a seizure or nerve pain medication that has also been used to reduce menopausal symptoms. It was originally developed for the treatment of epilepsy, and currently, gabapentin is widely used to relieve pain, especially neuropathic pain. The Neurontin™ had no impact on reducing the menopausal symptoms and was discontinued in August 2009. At this time, the patient was treated with Effexor™ (generic name Venlafaxine), a medication which is used primarily for the treatment of major depression, generalized anxiety disorder, social anxiety disorder, obsessive—compulsive disorder, panic disorder, and menopausal hot flashes in adults. The Effexor™ had no impact on reducing the menopausal symptoms and was discontinued in October 2009.

At this time, the patient began Wellbutrin™ again to treat the hot flashes, night sweats and other menopausal symptoms. The Wellbutrin™ had no impact on reducing the hot flashes, night sweats and other menopausal symptoms. Also at this time, she started Black Cohosh (an herbal remedy) to treat the indications, which had no impact on reducing the indications.

Dextromethorphan, e.g., Dextromethorphan HBr was then started January 2010 at a dose of 30 mg per day (15 mg every 12 hours), and the patient reported that the occurrence of hot flashes, night sweats and other menopausal symptoms were reduced significantly two days after starting the Dextromethorphan, e.g., Dextromethorphan HBr. After three days, the hot flashes, night sweats and other menopausal symptoms were drastically reduced and were totally gone by the third day. The dosage continued and remained the same for another 5 days.

With the patient's permission, the Dextromethorphan, e.g., Dextromethorphan HBr was then discontinued and the menopausal symptoms reoccurred within 24 hours. The symptoms were again eliminated within 24 hours after again commencing treatment with the Dextromethorphan, e.g., Dextormethorphan HBr. While continuing the treatment of Dextromethorphan, e.g., Dextromethorphan HBr and with the patient's permission, the Wellbutrin™ was discontinued and the hot flashes, night sweats and menopausal symptoms did not reoccur.

Example 2

Dextromethorphan, e.g., DextromethorphanHBr Resolved Hot Flashes in Menopausal Women with No Breast Cancer History The following Table summarizes data from female test subjects who had not had a breast cancer history but were experiencing symptoms of hormonal variation likely due to entering natural menopause. The dosage given in these test cases was 15 mg in the morning and 15 mg in the evening of Dextromethorphan, e.g., DextromethorphanHBr. The decrease in the symptoms of hormonal variation was noted by assessing the severity and frequency of hot flashes.

TABLE 1

Response of Dextromethorphan, e.g., DextromethorphanHBr in Menopausal Women with No Breast Cancer History

| Test Subject | Age | No. of Years with Hot Flashes | Frequency of Hot Flashes | Other Health Issues | Other Treatments Used Before With No Response | Response to Dex. HBr |
|---|---|---|---|---|---|---|
| 1 | 48 | 6 | 4 times/day 3 times/night | High blood pressure | Hormonal patch, Black Cohosh | No more hot flashes |
| 2 | 61 | 5-7 | 3-4 times/day, Approximately 2 times/night | Partial hysterectomy 25 years ago | Hormonal patch, Flashease, Amberen, Black Cohosh | No more hot flashes |

TABLE 1-continued

Response of Dextromethorphan, e.g., DextromethorphanHBr in
Menopausal Women with No Breast Cancer History

| Test Subject | Age | No. of Years with Hot Flashes | Frequency of Hot Flashes | Other Health Issues | Other Treatments Used Before With No Response | Response to Dex. HBr |
|---|---|---|---|---|---|---|
| 3 | 51 | Several | | None | | Moderate response (some reduction in hot flashes) |
| 4 | 50 | Several | | None | | No more hot flashes |
| 5 | 54 | 3-4 | | No major health issues | | No more hot flashes |

As can be seen from Table 1, the administration of Dextromethorphan, e.g., DextromethorphanHBr to five women without any breast cancer history, but with hormonal variation symptoms, relieved the symptoms as seen by a reduction in hot flashes. In fact, four out of the five women no longer had hot flashes when on Dextromethorphan.

Example 3

Standard Protocol to Administer a Pharmacologically Active Agent to Resolve Symptoms of Hormonal Variation The following example provides a protocol for the administration of a pharmacologically active agent, e.g., Dextromethorphan, to reduce, eliminate, or prevent the symptoms of hormonal variation.

Protocol:

Identify a subject having one or more symptoms of hormonal variation;

Administer to the subject a starting dosage of 15 mg of Dextromethorphan, e.g., DextromethorphanHBr in the morning and evening for a total dosage of 30 mg Dextromethorphan, e.g., DextromethorphanHBr;

Monitor the symptoms of hormonal variation, such as hot flashes.

If the symptoms remain or are lessened, an additional dosage of 15 mg Dextromethorphan, e.g., DextromethorphanHBr can be administered in the afternoon to try to eliminate the symptoms. Alternatively, the amount of Dextromethorphan, e.g., DextromethorphanHBr can be increased in the morning and evening. As is standard practice in the medical field, the dosage of compounds given may need to be adjusted for each subject depending on the subject's age, weight, gender, metabolism, etc.

If the symptoms are eliminated using the protocol delineated above, the dosage of Dextromethorphan, e.g., DextromethorphanHBr can be maintained or the dosage can be reduced to find the minimum dosage that will still eliminate the symptoms of the subject.

Example 4

Standard Protocol to Administer a Pharmacologically Active Agent Along with Gabapentin to Resolve Symptoms of Hormonal Variation The compounds of the invention can also be administered to a subject along with other compounds known to reduce, eliminate, or prevent hormonal variations. The following example provides a protocol for the administration of Dextromethorphan, e.g., DextromethorphanHBr, along with Gabapentin, a compound shown to reduce hot flashes in clinical trials.

Protocol:

Identify a subject having one or more symptoms of hormonal variations;

Administer to the subject a starting dosage of 15 mg of Dextromethorphan, e.g., DextromethorphanHBr and 300 mg of Gabapentin each in the morning and evening for a total dosage of 30 mg Dextromethorphan, e.g., DextromethorphanHBr and 600 mg of Gabapentin per day;

Monitor the symptoms of hormonal variation, such as hot flashes.

If the symptoms remain or are lessened, an additional dosage of 15 mg Dextromethorphan, e.g., DextromethorphanHBr and 300 mg of Gabapentin can be administered in the afternoon to try to eliminate the symptoms. Alternatively, the amounts of Dextromethorphan, e.g., DextromethorphanHBr and/or Gabapentin can be increased in the morning and evening.

If the symptoms are eliminated using the protocol delineated above, the dosage of Dextromethorphan, e.g., DextromethorphanHBr and Gabapentin can be maintained or reduced. For example, the subject may try to take only one dosage a day. As another example, the subject may opt to reduce the amount of each compound given in the morning and evening. As examples, the amount of gabapentin may be reduced to a lower level, such as 400 mg per day, 300 mg per day, 200 mg per day, 100 mg per day, 50 mg per day or even as low as 1 mg per day.

While the present invention has been illustrated by a description of various embodiments and while these embodiments have been described in considerable detail, it is not the intention of the Applicant to restrict, or any way limit the scope of the appended claims to such detail. The invention in its broader aspects is therefore not limited to the specific details, representative apparatus and method, and illustrative example shown and described. Accordingly, departures may be made from such details without departing from the spirit or scope of Applicant's general inventive concept.

What is claimed is:

1. A method for treatment of symptoms of hormonal variation, comprising:
    identifying a subject having one or more symptoms of hormonal variations resulting in hot flashes and night sweats; and
    administering an effective amount of Dextromethorphan or Dextrorphan, or a pharmaceutically acceptable salt thereof, to the subject, wherein the Dextromethorphan or Dextrorphan are the only active agents administered.

2. The method of claim 1 wherein said Dextromethorphan is DextromethorphanHBr.

3. The method of claim 1 wherein the effective amount of Dextromethorphan or Dextrorphan is from 0.1 to 120 mg per day.

4. The method of claim 1 wherein the subject is a female.

5. The method of claim 1 wherein the subject is a male.

* * * * *